(12) United States Patent
Haase et al.

(10) Patent No.: US 12,156,756 B2
(45) Date of Patent: Dec. 3, 2024

(54) FIELD OF VIEW MATCHING FOR MOBILE 3D IMAGING

(71) Applicant: KONINKLIJKE PHILIPS N.V., Eindhoven (NL)

(72) Inventors: Christian Haase, Hamburg (DE); Christian Buerger, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 258 days.

(21) Appl. No.: 17/782,871

(22) PCT Filed: Dec. 2, 2020

(86) PCT No.: PCT/EP2020/084187
§ 371 (c)(1),
(2) Date: Jun. 6, 2022

(87) PCT Pub. No.: WO2021/115855
PCT Pub. Date: Jun. 17, 2021

(65) Prior Publication Data
US 2023/0091213 A1    Mar. 23, 2023

(30) Foreign Application Priority Data
Dec. 10, 2019   (EP) .................................. 19214870

(51) Int. Cl.
*A61B 6/03* (2006.01)
*A61B 6/00* (2006.01)
(Continued)

(52) U.S. Cl.
CPC ............ *A61B 6/4441* (2013.01); *A61B 6/027* (2013.01); *A61B 6/032* (2013.01); *A61B 6/5241* (2013.01);
(Continued)

(58) Field of Classification Search
CPC ....... A61B 6/027; A61B 6/032; A61B 6/4405; A61B 6/4441; A61B 6/5241; A61B 6/547; G06T 11/005
See application file for complete search history.

(56) References Cited

U.S. PATENT DOCUMENTS

| | | |
|---|---|---|
| 2009/0074136 A1 | 3/2009 | Kamegawa |
| 2010/0014740 A1 | 1/2010 | Movassaghi |

(Continued)

OTHER PUBLICATIONS

International Search Report and Written Opinion of PCT/P2020/084187, dated Feb. 22, 2021.
(Continued)

*Primary Examiner* — Mark R Gaworecki

(57) ABSTRACT

The present invention relates to matching a field of view for mobile 3D imaging, for example mobile C-arm 3D imaging In order to provide image data that is improved for comparing purposes, for example when using a mobile X-ray imaging system, first location information of a first reconstruction volume based on a first sequence of X-ray images of a region of interest of a subject acquired along a first trajectory in a first position of an X-ray imaging device is received. Further, a planned second trajectory for acquiring a second sequence of X-ray images in a second position of the X-ray imaging device is received and a resulting second reconstruction volume for the second sequence of X-ray images is calculated. Then, second location information for the second reconstruction volume is determined. Further, a degree of comparability for the first reconstruction volume and the second reconstruction volume is determined based on the first location information and the second location information. An adapted second trajectory is calculated that results in an increased degree of comparability of the first reconstruction volume and the second reconstruction volume. The adapted second trajectory is provided for acquiring (Continued)

the second sequence of X-ray images in the second position of the X-ray imaging device.

20 Claims, 5 Drawing Sheets

(51) Int. Cl.
*A61B 6/02* (2006.01)
*G06T 11/00* (2006.01)

(52) U.S. Cl.
CPC ............ *A61B 6/547* (2013.01); *G06T 11/005* (2013.01); *A61B 6/4405* (2013.01)

(56) References Cited

U.S. PATENT DOCUMENTS

| | | | |
|---|---|---|---|
| 2015/0238159 A1 | 8/2015 | Al Assad |
| 2016/0166226 A1 | 6/2016 | Abkai |
| 2016/0345923 A1 | 12/2016 | Wakai |
| 2017/0035374 A1 | 2/2017 | Schafer |
| 2017/0311921 A1 | 11/2017 | Feuerlein |
| 2018/0368791 A1 | 12/2018 | Konig |

OTHER PUBLICATIONS

Tucker, Emerson et al "Towards Clinical Translation of Augmented Orthopedic Surgery: from Pre-Op CT to Intra-Op X-Ray via RGBD Sensing", Proceeding of SPIE Medical Imaging, 2018.
Fotouhi, Javad et al "Automatic Intraoperative Stitching of Nonoverlapping Cone-Beam CT Acquisitions", Medical Physics, vol. 45, No. 6, 20108. pp. 2463-2475, 2018.

FIELD OF VIEW MATCHING FOR MOBILE 3D IMAGING

CROSS-REFERENCE TO PRIOR APPLICATIONS

This application is the U.S. National Phase application under 35 U.S.C. § 371 of International Application No. PCT/EP2020/084187, filed on Dec. 2, 2020, which claims the benefit of European Patent Application No. 19214870.8, filed on Dec. 10, 2019. These applications are hereby incorporated by reference herein.

FIELD OF THE INVENTION

The present invention relates to matching a field of view for mobile 3D imaging. The present invention relates in particular to a device for optimizing an X-ray imaging trajectory, to an X-ray imaging system and to a method for optimizing an X-ray imaging trajectory.

BACKGROUND OF THE INVENTION

In surgery applications, mobile C-arm imaging systems are frequently used. As an example, motorized systems can be used to create a 3D volumetric reconstruction after a predefined sequence of projection images was recorded. Such an acquisition may be challenging since often many devices and systems, as well as clinical staff are present around the subject table. A further challenge may occur when a second 3D acquisition is to be performed to evaluate e.g. a procedure outcome or progress. A mobile C-arm can be moved freely by an operator, and may thus not be at the same position for a second acquisition as it was for the first acquisition, and it may be required to execute another trajectory. However, it has been shown that this may be cumbersome for comparing both reconstructed 3D volumes.

SUMMARY OF THE INVENTION

There may thus be a need to provide image data that is improved for comparing purposes.

The object of the present invention is solved by the subject-matter of the independent claims; further embodiments are incorporated in the dependent claims. It should be noted that the following described aspects of the invention apply also for the device for optimizing an X-ray imaging trajectory, for the X-ray imaging system and for the method for optimizing an X-ray imaging trajectory.

According to the present invention, a device for optimizing an X-ray imaging trajectory is provided. The device comprises a location information receiver, a processor and a trajectory adaptor. The location information receiver is configured to receive first location information of a first reconstruction volume based on a first sequence of X-ray images of a region of interest of a subject acquired along a first trajectory in a first position of an X-ray imaging device. The location information receiver is also configured to receive a planned second trajectory for acquiring a second sequence of X-ray images in a second position of the X-ray imaging device. The processor, coupled to the location information receiver and the trajectory adaptor, is configured to calculate a resulting second reconstruction volume for the second sequence of X-ray images. The processor is also configured to determine second location information for the second reconstruction volume. The processor is further configured to determine a degree of comparability for the first reconstruction volume and the second reconstruction volume based on the first location information and the second location information. The processor is still further configured to calculate an adapted second trajectory that results in an increased degree of comparability of the first reconstruction volume and the second reconstruction volume. For an optimized X-ray imaging trajectory, the trajectory adaptor is configured to provide the adapted second trajectory for acquiring the second sequence of X-ray images in the second position of the X-ray imaging device.

This provides improved comparability of the first and second reconstruction volume and thus provides improvement for comparing purposes.

In an example, for an optimized X-ray imaging trajectory, the adapted second trajectory is used in a mobile C-arm 3D imaging system.

According to an example, the degree of comparability is provided as an overlap degree of the first reconstruction volume and the second reconstruction volume.

According to an example, the overlap degree relates to a degree of a spatial overlap of the first reconstruction volume and the second reconstruction volume.

According to an example, the location information receiver is configured to receive spatial information of the X-ray imaging device during an acquisition of the first sequence of X-ray images along the first trajectory. The processor is configured to determine the first trajectory based on the spatial information, and to determine the resulting first reconstruction volume.

According to an example, the location information receiver is configured to receive a sequence of first images taken by a camera showing the X-ray imaging device during the acquisition of the first sequence of X-ray images along the first trajectory. The processor is configured to determine the first trajectory based on the sequence of images, and to determine the resulting first reconstruction volume.

According to the present invention, also an X-ray imaging system is provided. The system comprises an X-ray imaging device with an X-ray source and an X-ray detector movably along a trajectory to acquire a sequence of X-ray images of a region of interest. The system also comprises a device for optimizing an X-ray imaging trajectory according to one of the preceding examples. The X-ray imaging device provides the first sequence of X-ray images of a region of interest of a subject. Further, the trajectory adaptor provides the adapted second trajectory to the X-ray imaging device for acquiring the second sequence of X-ray images in the second position of the X-ray imaging device.

According to an example, the X-ray imaging system is a mobile X-ray system with a base freely movable along a floor surface. The X-ray imaging device comprises a movable C-arm with the X-ray source and the X-ray detector mounted to opposing ends of the C-arm. Further, a drive mechanism is provided for moving the C-arm to move the X-ray source and the X-ray detector along the adapted second trajectory.

The X-ray system may be provided as a mobile C-arm 3D imaging system.

According to an example, at least one optical camera is provided to provide a sequence of first images taken showing the X-ray imaging device during the acquisition of the first sequence of X-ray images along the first trajectory. The processor determines the first trajectory based on the sequence of images and determines the resulting first reconstruction volume.

According to the present invention, also a method for optimizing an X-ray imaging trajectory is provided. The method comprises the following steps:

receiving first location information of a first reconstruction volume based on a first sequence of X-ray images of a region of interest of a subject acquired along a first trajectory in a first position of an X-ray imaging device;

receiving a planned second trajectory for acquiring a second sequence of X-ray images in a second position of the X-ray imaging device;

calculating a resulting second reconstruction volume for the second sequence of X-ray images;

determining second location information for the second reconstruction volume;

determining a degree of comparability for the first reconstruction volume and the second reconstruction volume based on the first location information and the second location information;

calculating an adapted second trajectory that results in an increased degree of comparability of the first reconstruction volume and the second reconstruction volume; and providing the adapted second trajectory for acquiring the second sequence of X-ray images in the second position of the X-ray imaging device.

According to an aspect, in an example, it is provided that based on external camera images, the field of view for a planned 3D volumetric reconstruction is estimated before the corresponding projection sequence is acquired. The estimated field of view for a planned 3D volumetric reconstruction is compared to a previous 3D reconstruction and it is assessed if sufficient overlap of diagnostically relevant areas is given. The planned trajectory for the planned 3D volumetric reconstruction is adapted in order to improve the overlap of the estimated reconstruction field of view with a previous acquisition. A visual indicator may provide feedback to the clinician in case the C-arm system needs to be repositioned in order to create a second 3D reconstruction with sufficient overlap with a first 3D reconstruction.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
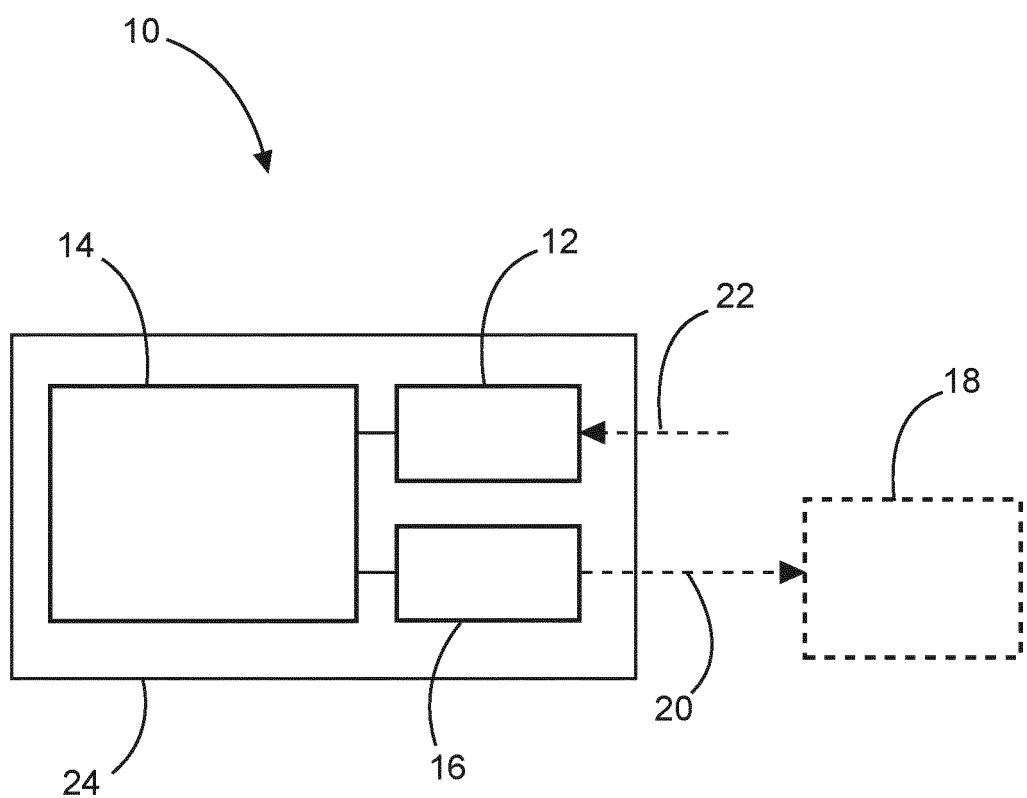
FIG. 1 shows an example of a device for optimizing an X-ray imaging trajectory.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

Mobile X-ray imaging systems are frequently used in surgery applications. Motorized systems can be used for achieving 3D volumetric reconstruction after a predefined scan or sequence of projection images was recorded along a certain trajectory. This movement along the trajectory may be challenging since often many devices and systems, as well as clinical staff are present around the subject table. For such X-ray imaging, fixedly installed systems with movable components are provided as well as mobile systems, like mobile C-arm imaging systems. If imaging is required that allows comparison, similar images may be helpful for the clinical staff. As an example, a second 3D acquisition is to be performed to evaluate e.g. the procedure outcome or progress. Pre- and post-surgery volumetric 3D reconstructions may not show the same 3D region of interest since the positioning of the C-arm, the subject, or the surrounding obstacles may have changed. As another example, since a mobile C-arm can be moved freely by the operator, the system might not be at the same position for the second acquisition as for the first acquisition. If both reconstructed 3D volumes are to be compared, this may be cumbersome or may even be a problem.

The term "subject" may also be referred to as individual. The "subject" may further also be referred to as patient, although it is noted that this term does not indicate whether any illness or disease is actually present with the subject.

FIG. 1 shows an example of a device 10 for optimizing an X-ray imaging trajectory. The device 10 comprises a location information receiver 12, a processor 14 and a trajectory adaptor 16. The location information receiver 12 is configured to receive first location information of a first reconstruction volume based on a first sequence of X-ray images of a region of interest of a subject acquired along a first trajectory in a first position of an X-ray imaging device. The location information receiver 12 is also configured to receive a planned second trajectory for acquiring a second sequence of X-ray images in a second position of the X-ray imaging device. The processor 14, coupled to the location information receiver 12 and the trajectory adaptor 16, is configured to calculate a resulting second reconstruction volume for the second sequence of X-ray images. The processor 14 is also configured to determine second location information for the second reconstruction volume. The processor 14 is further configured to determine a degree of comparability for the first reconstruction volume and the second reconstruction volume based on the first location information and the second location information. The processor 14 is still further configured to calculate an adapted second trajectory that results in an increased degree of comparability of the first reconstruction volume and the second reconstruction volume. For an optimized X-ray imaging trajectory, the trajectory adaptor 16 is configured to provide the adapted second trajectory for acquiring the second sequence of X-ray images in the second position of the X-ray imaging device.

As a result, the trajectory is optimized, instead of moving the complete X-ray imaging device. The goal is to improve the comparison, which also comprises to accept a degree of uncertainty. A sort of compromise is trying to be achieved.

The term "location information" relates to information about the spatial position of the respective reconstruction volume. In order to assess the degree of comparability, e.g. a spatial overlap of the two reconstruction volumes, i.e. in order to compare the two reconstruction volumes, the spatial position at least indirectly refers to the same spatial reference. For example, the spatial position of the first reconstruction volume may relate to reference coordinates of the imaging device in the first position, and the spatial position of the second reconstruction volume may relate to reference coordinates of the imaging device in the second position, whilst the displacement between the first and the second position is also provided (or determined). The spatial position provides information about the three-dimensional arrangement and rotation. As an example, the location information may be provided in relation to a fixed base within an examination room, for example a reference point of a 3D coordinate grid inside the examination room. As another example, the location information may be provided in relation to a moving base within an examination room, such as a subject support, e.g. a patient table.

The term "reconstruction volume" relates to a region for which data is available that can be used for reconstructing image data for that volume. As an example, a plurality of image projections is provided that relate to different imaging directions. The 3D volumes that are traversed by the projection rays sufficiently overlap such that it is possible to retrieve the 3D data from the 2D projections. As an example, the reconstruction volume relates to an area of the subject for which image data is generated for example by computed tomography. The reconstruction volume is also referred to as 3D-field of view.

The first reconstruction volume is also referred to as previous reconstruction volume, and the second reconstruction volume as estimated reconstruction volume.

In an example, the first reconstruction volume relates to a pre-operational scenario, and the second reconstruction volume relates to post-operational scenario. An examination, intervention, treatment or other procedure may have taken place between the pre-operational scenario and the post-operational scenario.

The term "trajectory" relates to the paths in space along which an image source and an image detector are moving for acquiring a plurality of projections to cover the region of interest from different directions in order to be able to generate the 3D image data of the region of interest. In an example, the "trajectory" relates to the movement of a C-arm (also referred to as C-arc) and the respective movement paths of the source and detector mounted to the C-arm. The trajectory may be a rotation motion, a sliding motion along an arc, a swiveling motion or any combination provided by the respective bearing and support concepts of the C-arm.

The first trajectory is also referred to as initial trajectory. The second trajectory is also referred to as the upcoming trajectory or planned trajectory, and the adapted second trajectory as adapted upcoming trajectory, adapted planned trajectory or adapted trajectory.

In an example, the planned second trajectory is provided as the first trajectory for the second position of the X-ray imaging device.

The term "planned" relates to the second trajectory as defined before the adaptation. For example, the planned trajectory may be the same trajectory (for example, in relation to a base) as used for the first scan. However, due to a misalignment of the X-ray imaging device between the first and the second position, the resulting reconstruction volumes would not identically match. Rather, a deviation of the first and the second reconstruction volume is to be expected. In another example, the planned trajectory may be a predefined trajectory (for example, in a certain, predefined relation to a base), but due to a possible misalignment of the X-ray imaging device between the first and the second, planned position, the resulting reconstruction volumes would also not identically match.

The term "degree of comparability" relates to the spatial position and orientation of the two reconstruction volumes, i.e. the first and the second reconstruction volumes, and their resulting capability (or suitability) for comparing the first and the second reconstruction volumes, i.e. for comparing projections of the first and the second reconstruction volumes.

The term "degree of comparability" thus also relates to a degree of similarity in view of the comparison.

In an example, the degree of comparability is provided as a degree of overlap, also referred to as overlap degree.

The term "overlap degree" relates to the spatial position and orientation of the two reconstruction volumes, i.e. the first and the second reconstruction volumes. For example, the overlap is determined as a spatial overlap, i.e. an overlap in 3D space. The overlap can be defined as those positions in space that are covered by both reconstruction volumes.

The term "adapted" relates to a modification of the second trajectory according to the target to improve the overlap, despite a misalignment of the first and the second position of the X-ray imaging device. The second trajectory may be used as a starting point and the trajectory may then be modified, i.e. changed, such that an improved spatial overlap is provided.

In an example, the second position of the X-ray imaging device remains for the adapted trajectory. Instead of modifying the position and orientation of the X-ray imaging device, such as a mobile base, the trajectory is modified at least within the given geometrical constraints, while the position of the X-ray imaging device is not changed.

The term "position" of the X-ray imaging device relates to an arrangement, or location of the parts of the X-ray imaging device that are not moving during the imaging scan.

In an example, the adaptation of the planned trajectory is provided in an automated manner.

In an example, the location information receiver is configured to receive a first trajectory used for the first reconstruction volume. The processor is configured to determine a resulting first reconstruction volume.

As an example, the planned second trajectory is the same trajectory as the first trajectory, but (theoretically or virtually) applied to the second position or second location of the X-ray imaging device. The planned second trajectory is then adapted to achieve better matching volume of interests, i.e. reconstruction volumes, which adaptation results in the adapted second trajectory, which is then used for performing the second scan.

In an example, the location information receiver is configured to receive location information for the second position of the X-ray imaging device. For the planned second trajectory, the processor is configured to apply the first trajectory for the second position of the X-ray imaging device.

In an example, the location information receiver is configured to receive location information for the second reconstruction volume when applying the planned second trajectory.

In an example, the location information receiver is configured to receive location information for a planned second reconstruction volume and, for the planned second trajectory, a trajectory is computed that results in achieving the planned second reconstruction.

In an example, the planned second trajectory is a trajectory manually provided by a staff member.

In another example, the planned second trajectory is a trajectory proposed by the processor in view of avoiding possible collisions in a current situation.

In another example, the trajectory is timed relative to a breathing motion, a heart motion or a contrast agent motion. Thus, comparability is improved if the recorded heart phases, or contrast agent levels, etc. are comparable in the two scans. If the scans show slightly different areas of the body, the contrast arrival time may be different. Or if the second scan starts from a different position on the same circle as the first scan, a synchronization with e.g. heart beats may still be off. This may then even require an additional input. The trajectory could accordingly be slowed down initially.

In FIG. 1, a display or interface 18 (shown in dashed lines) is provided as an option, configured to display information about the adapted second trajectory to an operator.

Further, a first arrow 20 (shown in dashed lines) indicates a data output, i.e. a data connection.

A second arrow 22 (shown in dashed lines) indicates a data input. A frame 24 surrounding the location information receiver 12, the processor 14 and the trajectory adaptor 16, indicates that the information receiver 12, the processor 14 and the trajectory adaptor 16 can be provided integrated into a common structure like a common housing. In an example, the information receiver 12, the processor 14 and the trajectory adaptor 16 are provided in an integrated manner. In another example, the information receiver 12, the processor 14 and the trajectory adaptor 16 are provided separately.

In an option, it is provided that the degree of comparability is provided as an overlap degree of the first reconstruction volume and the second reconstruction volume.

In a further option, it is provided that the overlap degree relates to a degree of a spatial overlap of the first reconstruction volume and the second reconstruction volume.

In an example, a part of the first reconstruction volume is selected as first reference portion and a part of the second reconstruction volume is selected as second reference portion; the overlap is determined based on the first reference portion and the second reference portion.

In an example, for the first location information, the location information receiver 12 is configured to receive a first trajectory and its spatial location; and the processor 14 is configured to determine the resulting first reconstruction volume and the first location information of the first reconstruction volume based on the first trajectory and its spatial location.

In an example, the location information receiver 12 is configured to receive spatial information of the X-ray imaging device during an acquisition of the first sequence of X-ray images along the first trajectory; and the processor 14 is configured to determine the first trajectory based on the spatial information, and to determine the resulting first reconstruction volume.

In an example, the location information receiver 12 is configured to receive a sequence of first images taken by a camera showing the X-ray imaging device during the acquisition of the first sequence of X-ray images along the first trajectory; and the processor 14 is configured to determine the first trajectory based on the sequence of images, and to determine the resulting first reconstruction volume.

In an example, the X-ray imaging device comprises a movable C-arm and the images show the movement of the C-arm.

In an example, the X-ray imaging system is a mobile X-ray imaging system, and, for the first position of the X-ray imaging device, a first position of the X-ray imaging system is determined based on the images taken by the camera. Further, for the second position of the X-ray imaging device, a second of the X-ray imaging system is determined based on at least one second image taken by the camera showing the X-ray imaging device before an acquisition of the second sequence of X-ray images.

The mobile X-ray system, for an example a movable C-arm mounted to a carriage, is provided with a number of degrees of freedom to move. In an example, the system is not motorized in relation to the floor and the movement along the floor is also not tracked. The difference in position between the first position and the second position are detected based on an external detection system, such as cameras providing an optical tracking system. In another example, electromagnetic tracking is provided to track the first and second position within an examination room.

In an example, a subject on a subject support is also tracked by an optical camera. In an option, the subject is tracked by images. In another option, the subject is tracked by electromagnetic tracking.

In order to compare the first and the second reconstruction volume, the first scan movement is captured by one or more cameras. In an example, the cameras capture where the first reconstruction volume is located. After a relative movement of imaging device and subject, a repetition of the same scan movement would lead to a second reconstruction volume that would be offset, i.e. displaced.

By changing, i.e. adapting the trajectory for the (second) scan, an improvement is achieved by providing a second reconstruction volume that is having more overlap compared to when applying the non-adapted trajectory. At least to a certain extent, this avoids the need for providing instructions to an operator, e.g. a doctor or nurse, to move the X-ray imaging device. The adapted second trajectory thus replaces relocation instructions. Following, the imaging procedure is facilitated, and the staff members are relieved from a further task.

With regards to X-ray imaging, an information or warning that the current position is not suitable for imaging, may be considered as first step or stage of support. While the provision of instructions how to achieve an improved position of the X-ray imaging (i.e. a relation guidance) may be considered as second step or stage of support, the provision of an adapted trajectory may be considered as third step or stage of support.

External cameras may thus be used to estimate and verify that two 3D reconstruction field of views have sufficient overlap for diagnostic purposes. The overlap may be improved by using the camera information to define a specific trajectory for the second acquisition, or by an indication to the operator to change the starting position of the system.

The external cameras may be provided on the system or in the operating room. The external cameras may also be used for facilitating the finding of an optimal trajectory around all obstacles while still acquiring projections from all needed angulations.

In an example, the movement of the X-ray imaging between the first and the second position is detected by driving wheels, or sensors in bearings that provide spatial information of a movement.

In an example, the first location information comprises first subject-related spatial information in the first position of the X-ray imaging device. The location information receiver 12 is configured to receive second subject-related spatial information in the second position of the X-ray imaging device; and the processor 14 is configured to determine the overlap degree of the first reconstruction volume and the second reconstruction volume in relation to the subject.

This provides the effect that the overlap is assessed in view of the intended use of the image data comparison.

The (first and second) reference portions may also be referred to as (first and second) core regions of interest within the (first and second) regions of interest covered by the (first and second) reconstruction volumes.

In an example, the processor 14 is configured to determine if the degree of comparability is outside of a predetermined range of comparability. A repositioning indicator is provided configured to indicate that a repositioning of the X-ray imaging device is required.

As an example, a minimum overlap of 30% is provided. In a further example, the minimum is 50%.

In an example, for determining and assessing the degree of the overlap, also a type of the imaging task is considered. For example, for certain imaging purposes, the degree of overlap required may be less.

In a further example, the reconstruction volumes are both cylindric regions, and the overlap results in a spherical region.

In a further example, the reconstruction volumes are both cylindric regions that are arranged perpendicular to each other.

For example, a C-arm imaging is provided. The first and the second position are having a crosswise orientation of the imaging device, such as first position on the side of a patient support and the second position at the end of the subject support, or vice versa. One trajectory would then be defined by a propeller movement of the C-arm and the other trajectory would be defined as a roll movement of the C-arm.

In an example, the first and second position of the X-ray imaging device relate to an arrangement of the X-ray imaging device in relation to the subject. The second position is different from the first position.

The difference may result from a movement of the X-ray imaging device. The difference may also result from a movement of the subject to be imaged. The difference may as well result from a movement of both the X-ray imaging device and the subject to be imaged.

For example, the subject may be arranged in a different posture after an intervention or treatment. In another example, the X-ray imaging device may be moved away for an intervention or treatment and is them moved back for a further imaging procedure, but with at least a slight deviation in the position and/or orientation.

In an example, the subject is provided in a first posture during the first sequence of X-ray images. Further, the subject remains in the first posture also during the second sequence of X-ray images. The X-ray imaging device is arranged in a first location during the first sequence of X-ray images. Further, during the second sequence of X-ray images the X-ray imaging device is arranged in a second location.

In another example, the subject is provided in a first posture during the first sequence of X-ray images and in a second posture during the second sequence of X-ray images. The X-ray imaging device is arranged in a first location during the first sequence of X-ray images and remains in the first location also during the second sequence of X-ray images.

Figure 2:
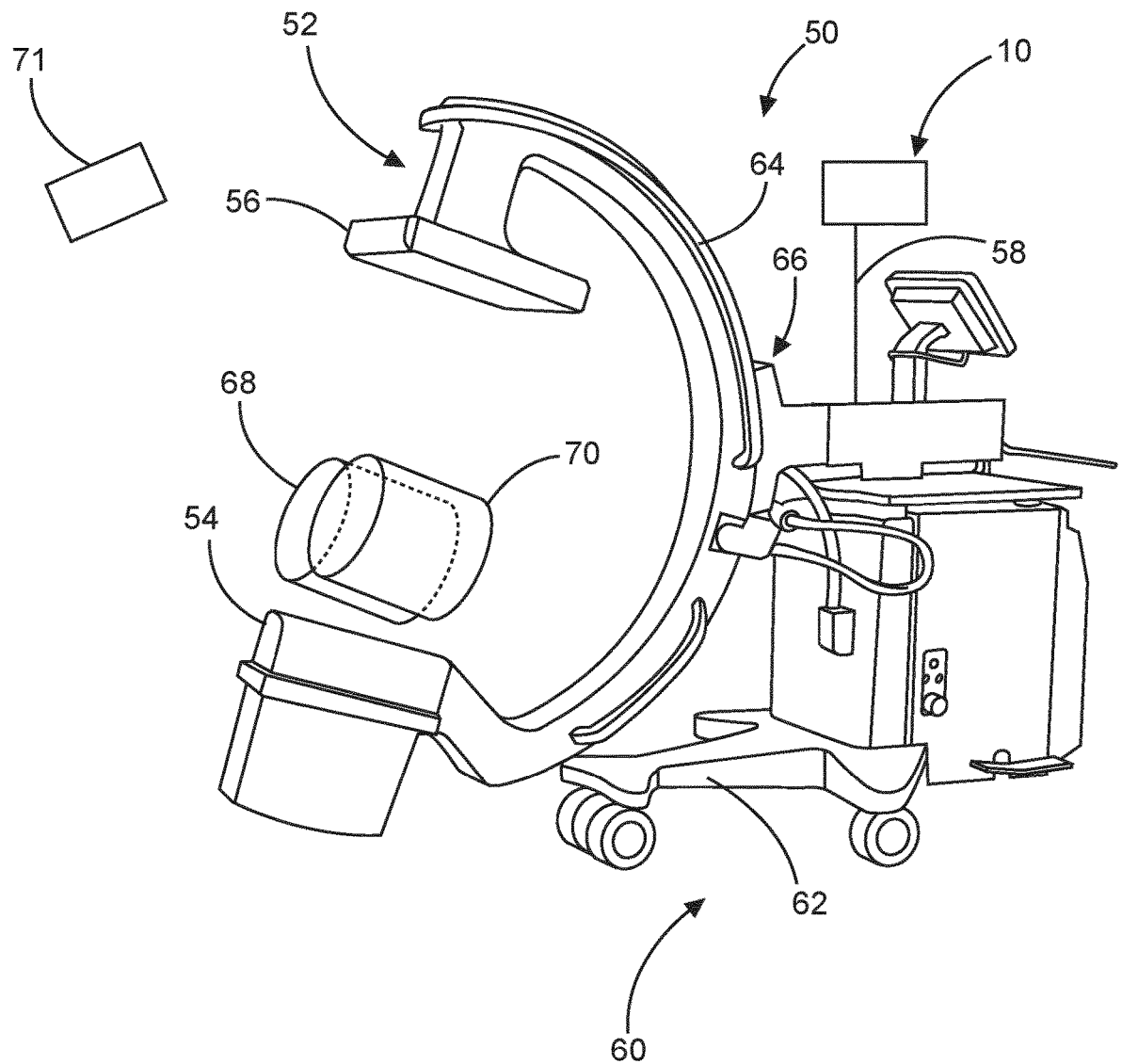
FIG. 2 shows an example of an X-ray imaging system.

In a further example, the subject is provided in a first posture during the first sequence of X-ray images and in a second posture during the second sequence of X-ray images. The X-ray imaging device is arranged in a first location during the first sequence of X-ray images and in a second location during the second sequence of X-ray images. FIG. 2 shows an example of an X-ray imaging system 50. The system 50 comprises an X-ray imaging device 52 with an X-ray source 54 and an X-ray detector 56 movably along a trajectory to acquire a sequence of X-ray images of a region of interest. Further, the system 50 comprises an example of the device 10 for optimizing an X-ray imaging trajectory according to one of the preceding examples. The device 10 is shown schematically as a separate frame, as an example. The device 10 can be provided in a separate housing or in an integrated manner. A line 58 indicates a data-connection between the X-ray imaging device 52 and the device 10 for optimizing an X-ray imaging trajectory. The X-ray imaging device 52 provides the first sequence of X-ray images of a region of interest of a subject. The trajectory adaptor 16 provides the adapted second trajectory to the X-ray imaging device 52 for acquiring the second sequence of X-ray images in the second position of the X-ray imaging device 52.

As an effect, the projections of the two 3D volumes generated based on the respective scan along the X-ray imaging trajectory are not influenced by small motion of the C-arm or the imaged object between the first and the second scan due to the adaptation of the trajectory.

In an example, shown as an option in FIG. 2, the X-ray imaging system 50 is a mobile X-ray system 60 with a base 62 freely movable along a floor surface. The X-ray imaging device 52 comprises a movable C-arm 64 with the X-ray source 54 and the X-ray detector 56 mounted to opposing ends of the C-arm 64. A drive mechanism 66 is provided for moving the C-arm 64 to move the X-ray source 54 and the X-ray detector 56 along the adapted second trajectory.

In FIG. 2, a first reconstruction volume 68 and a second reconstruction volume 70 are indicated. As can be seen, the two volumes 68, 70 partly overlap.

The first reconstruction volume 68 indicates a result from a first scan of a subject (for example arranged on a subject support (not further shown), while the X-ray imaging system 50 was arranged in a first location in relation to the subject. For example, the first scan has already been performed.

The second reconstruction volume 70 indicates a result from a second scan of the subject (for example also arranged on the subject support (not further shown), while the X-ray imaging system 50 is arranged in a second location in relation to the subject. For example, the second scan will be performed as next step.

The first and reconstruction volumes 68, 70 are indicated in a free-floating manner for indicating the overlap and thus the achievable comparability. In an example, the mobile X-ray system comprises a motor driven support wheel arrangement, and the support wheel arrangement provides location information for the second position of the X-ray system.

In an example, the X-ray imaging system is a fixed X-ray system comprising a movable support structure for the C-arm. The movable support structure provides location information for the second position of the X-ray system.

In an option, also shown in FIG. 2, at least one optical camera 71 is provided to provide a sequence of first images taken showing the X-ray imaging device during the acquisition of the first sequence of X-ray images along the first trajectory. The camera s is data connected to the device 10 for optimizing an X-ray imaging trajectory. The processor determines the first trajectory based on the sequence of images and determines the resulting first reconstruction volume.

Figure 5A:
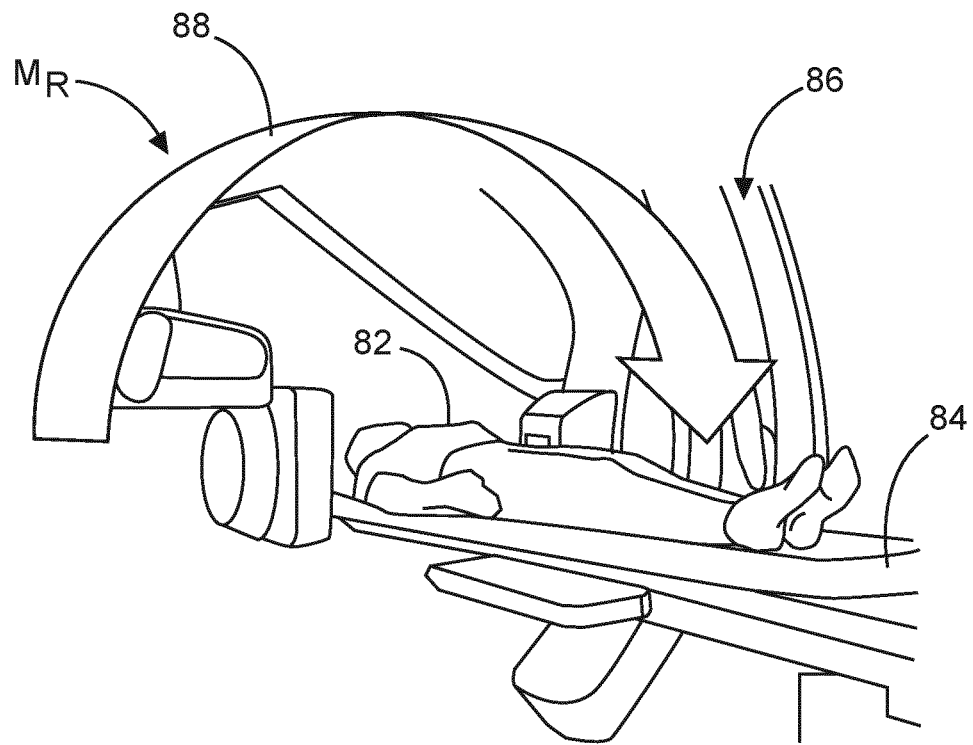
FIG. 5a shows an example for a planned second trajectory.
Figure 5B:
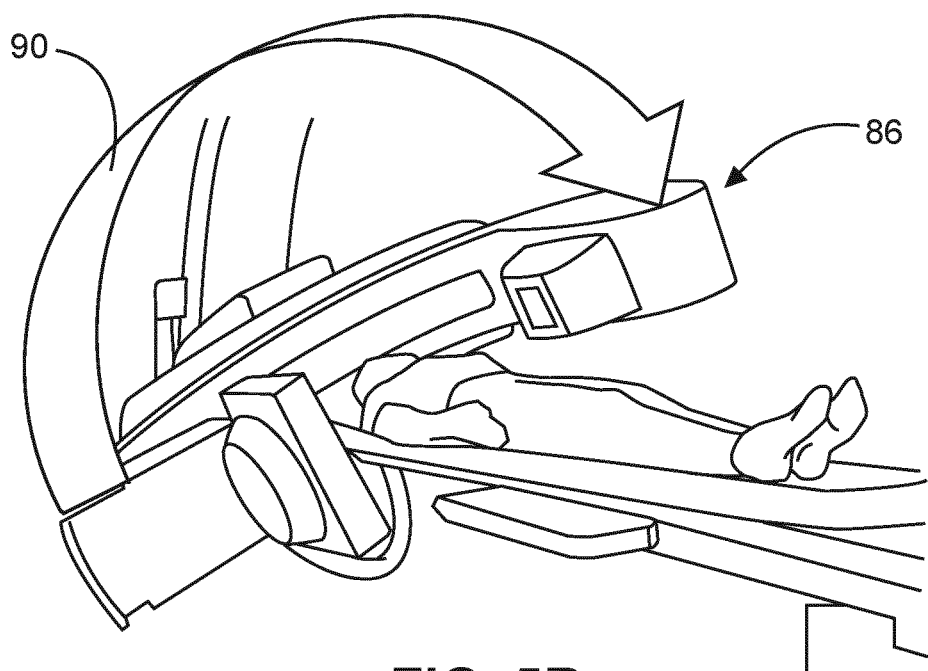
FIG. 5b shows an example of an adapted second trajectory.

It is noted that the at least one camera is not further shown in FIGS. 5A and 5B. The camera thus captures, i.e. detects, where the first reconstruction volume is arranged. The camera also captures, i.e. detects, where the second reconstruction volume would be arranged with adaptation.

Figure 3A:
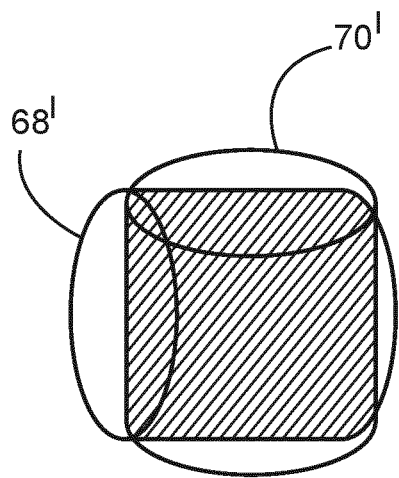
FIG. 3a and FIG. 3b show two examples of overlapping reconstruction volumes.
Figure 3B:
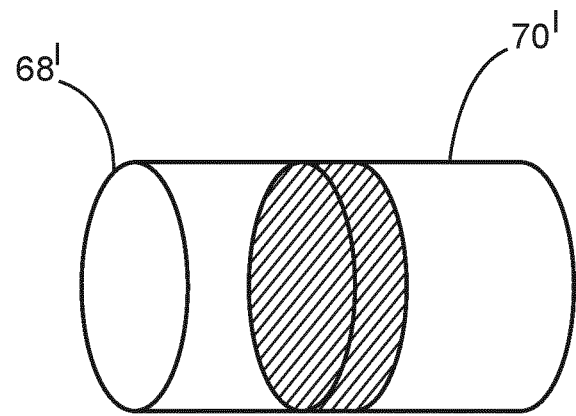

FIG. 3a and FIG. 3b show two further examples of overlapping reconstruction volumes. In the example shown in FIGS. 3a and 3b, a first cylindrical reconstruction volume 68', 68" and a second cylindrical reconstruction volume 70', 70" are provided that overlap in the middle.

In a first option, shown in FIG. 3a, the two cylinders, i.e. the cylindrical reconstruction volumes 68', 70', are oriented perpendicular to each other.

In a second option, shown in FIG. 3b, the two cylinders, i.e. the cylindrical reconstruction volumes 68" and 70", have the same orientation. For example, the underlying projections are recorded in similar directions.

The actual spatial overlap may thus be smaller in the second option (FIG. 3b) than in the first option (FIG. 3a), but the second option may still have a higher degree of comparability since the projection directions were similar. In this example only a small core area is of interest. Thus, a larger special overlap does not improve comparability. But the fact that the projection directions in the second option are similar, improves comparability since directional imaging artefacts (partial volume, beam hardening, scatter, metal streaks, etc.) and absolute voxel values (e.g. Hounsfield units) will be better comparable. Improved comparability in this example does not mean improved spatial overlap but an improved comparability of the tissue's X-ray attenuation properties that are recorded in the two reconstructed images.

Figure 4A:
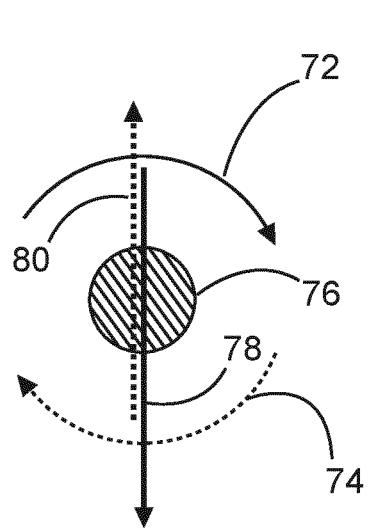
FIG. 4a and FIG. 4b show two examples of overlapping scan trajectories.
Figure 4B:
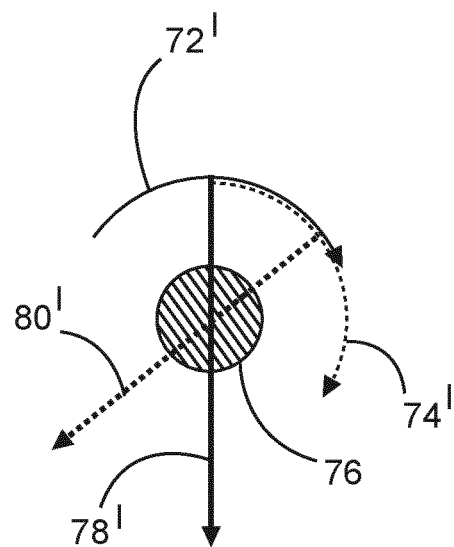

FIG. 4a and FIG. 4b show a first scan path 72, 72' and a second scan path 74, 74' around a region of interest 76 of a subject, where for the first and the second reconstruction volumes, a limited angular segment is used. The scan directions are indicated with curved, i.e. circular arrows. Resulting directions of partial angle artefacts of the first and the second scans are indicated with a first straight arrow 78, 78' for the first scan, and a second straight arrow 80, 80' for the second scan.

In FIG. 4a, the scan directions are in opposite directions, with resulting artefacts direction in opposite directions.

In FIG. 4b, the scan directions are the same, but with different angles. The resulting artefacts directions are arranged in angular manner.

In an option, the limited angular segments are as similar as possible, or at least in opposing directions. In this example the comparability is improved since the artefact directions are more similar.

FIG. 5a and FIG. 5b indicate a subject 82 arranged on a subject support 84. A movable C-arm X-ray imaging device 86 is partly shown. The C-arm can be moved such that the X-ray source and X-ray detector are rotated around the subject's area of interest, thus forming an ISO-center.

FIG. 5a shows an example for a planned second trajectory 88, which would result in a second reconstruction volume that would overlap with a first reconstruction volume, but only with a rather low degree of comparability.

FIG. 5b shows an example of an adapted second trajectory 90, which would result in an improved degree of comparability. In the example shown, the scan is provided around the subject 82 arranged on the subject support 84. The initially planned second trajectory, shown in FIG. 5a, is shown as a circular roll movement $M_R$ around the subject 82. The adapted second trajectory, shown in FIG. 5b, is shown as a propeller movement $M_P$ around the subject 82. A second reconstruction volume is thus achievable that has a better matching degree with the first reconstruction volume. The change from a roll movement $M_R$ to a propeller movement $M_P$ is an example for an adaptation of the second trajectory.

Figure 6:
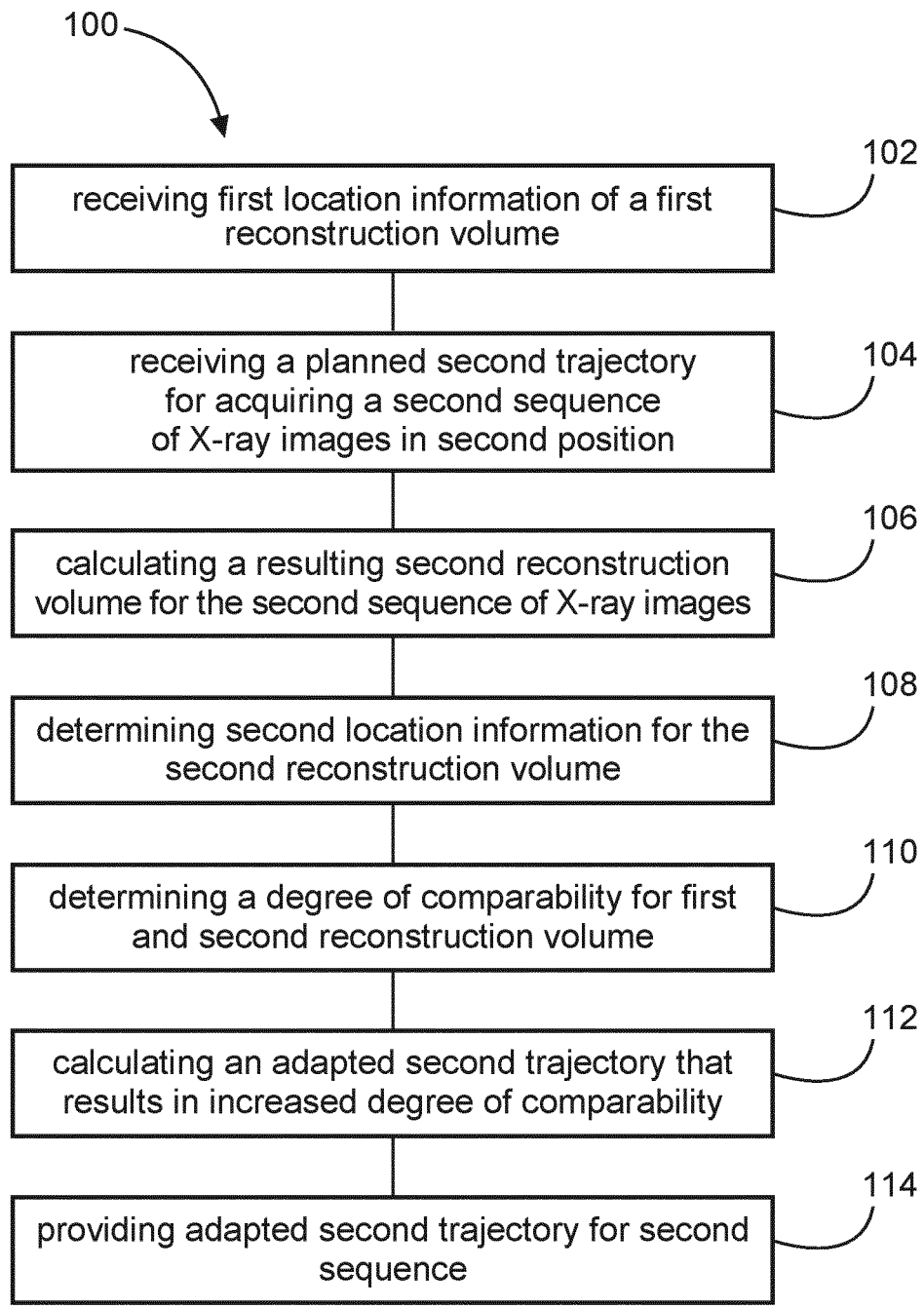
FIG. 6 shows basic steps of an example of a method for optimizing an X-ray imaging trajectory.

FIG. 6 shows basic steps of an example of a method 100 for optimizing an X-ray imaging trajectory. The method 100 comprises the following steps:

In a first step 102, also referred to as step a), first location information of a first reconstruction volume based on a first sequence of X-ray images of a region of interest of a subject acquired along a first trajectory in a first position of an X-ray imaging device is received.

In a second step 104, also referred to as step b), a planned second trajectory for acquiring a second sequence of X-ray images in a second position of the X-ray imaging device is received.

In a third step 106, also referred to as step c), a resulting second reconstruction volume for the second sequence of X-ray images is calculated.

In a fourth step 108, also referred to as step d), second location information for the second reconstruction volume is determined.

In a fifth step 110, also referred to as step e), a degree of comparability for the first reconstruction volume and the second reconstruction volume is determined based on the first location information and the second location information.

In a sixth step 112, also referred to as step f), an adapted second trajectory is calculated that results in an increased degree of comparability of the first reconstruction volume and the second reconstruction volume.

In a seventh step 114, also referred to as step g), the adapted second trajectory is provided for acquiring the second sequence of X-ray images in the second position of the X-ray imaging device.

The first step 102 of receiving the first location information and the second step 104 of receiving the planned second trajectory can also be provided simultaneously, or the second step 104 may be provided before the first step 102.

In an example, for the first location information, the first trajectory and its spatial location is provided and the resulting first reconstruction volume and the first location information of the first reconstruction volume are determined based on the first trajectory and its spatial location.

In an example, the first location information also comprises first subject-related spatial information in the first position of the X-ray imaging device. Further, second subject-related spatial information in the second position of the X-ray imaging device is provided. The degree of comparability, e.g. an overlap degree of the first reconstruction volume and the second reconstruction volume is determined in relation to the subject.

As an example, based on camera(s), e.g. external cameras, the detector and source trajectory of an 3D X-ray acquisition relative to the subject that is imaged is recorded. In an option, the camera(s) are fixed placed in the operating room or attached onto the C-arm with a view onto the patient. This may be facilitated by special markers on the C-arm system and/or the patient to capture and track the motion and movement. It may also be facilitated by natural features identifiable in the camera images. As dedicated markers, one or more QR-code markers may be attached to one or more dedicated positions on the detector, the source and/or the subject. E.g. centrally on each side of the detector housing, each side of the tube housing, and on the subject's skin. Natural markers that can be extracted from images can be a multitude of image features that can be recognized from different perspectives. E.g. edges, ridges, corners, markings, on the tube and detector housing. For the subject, features such as their eyes, fingers, wrinkles, skin spots, belly button, etc. may be used.

Based on the trajectory, the 3D field of view to be acquired relative to the patient anatomy is estimated. This can be done by tracking optical image features using the above special or natural markers according to the following: Multiple optical images are acquired when executing the first trajectory. In each image, image features can be detected and can be correlated to other optical images that were acquired from a different perspective. For instance, as another option, the camera is attached to the C-arm and the camera "looks" onto the patient when executing the first trajectory. In one image we can e.g. detect the patient's fingertip. Then the C-arm is moved along the first trajectory and further optical images are acquired. In all of those images, an attempt is made to find the patient's fingertip, now from different perspectives. All detected fingertips from different views can by matched and hence the patient's fingertip can be positioned in 3D space (relative to the C-arm). By repeating this method for all possible markers, it is possible to generate a point cloud, i.e. a cloud of numeral points, of 3D marker positions.

Further, for a second acquisition, a planned C-arm trajectory for a second 3D acquisition is calculated.

Based on the second planned trajectory the second 3D field of view to be acquired is estimated relative to the patient anatomy. In this step the detection of 3D marker positions as above is repeated.

Then, the overlap of the first 3D field of view and the second 3D field of view is calculated. This can be achieved by computing the overlap between the point clouds of all 3D marker positions from the first acquisitions with the ones from the second acquisition, i.e. there need to be enough feature correspondences between both point clouds. In other words, it is analyzed if sufficient overlap for a predefined diagnostic purpose is provided. The term sufficient overlap may depend on the desired diagnostic purpose. It may be represented by a volumetric percentage, if e.g. a general property like tissue iodine concentration is to be investigated. It may also be defined by specific anatomical landmarks that must all be within the overlapping volume i.e. all anatomical landmarks needed for a specific purpose. E.g. two specific vertebrae of interest must be fully in the overlapping field of view in order to compare them in the two images. Or specific points of interest (lesions, bifurcations, implants, aneurisms) within a vascular structure must all be contained in the overlapping volume.

If the overlap is not sufficient, a corrective action may be triggered, either by adjusting the planned trajectory or by giving an indication to the operator. For instance, depending on the motion degrees of freedom of the system, the user is advised to manually change the C-arm position so that a second trajectory can be executed with improved overlap to the first one.

An automatic trajectory adaptation will depend on the motorized degrees of freedom that can be controlled on the mobile C-arm unit. E.g. if motorized translations can be performed, the C-arm is positioned so that the iso-centers of the two acquisitions are as close as possible.

If the first trajectory was a roll movement of the C-arm, and the repositioned C-arm before the second acquisition is in a significantly different orientation, a propeller movement for the second acquisition may be preferable in order to better align the source and detector trajectory in 3D space. This will result in a better overlap of the reconstruction volume. Also, a combination of roll and propeller movements may be the solution to optimize the second trajectory.

In case of a limited angle reconstruction (less than 180° plus fan angle), the directions that are not imaged in each acquisition should ideally be identical. Depending on the repositioning of the C-arm, this may however mean different motor movement.

Different dual axis trajectories may be used to reconstruct the same 3D volume. If a new obstruction is placed in the path of the original trajectory in the second acquisition, a second dual axis trajectory may be chosen to image the same volume but avoiding the obstruction.

In case the C-arm repositioning does not permit to automatically acquire projections from sufficient angles of the initial reconstruction volume for a full second reconstruction, the second acquisition may be reduced to a limited angular segment. I.e. only the angular segment is imaged which also has the first reconstruction volume in the field of view. Then a limited angle reconstruction of the initial volume can be created for comparison. The acquisition of unnecessary data, i.e. data that does not relate to the first acquisition, during the second acquisition is avoided.

The present invention relates to matching a field of view for mobile 3D imaging, for example mobile C-arm 3D imaging. In order to provide image data that is improved for comparing purposes, for example when using a mobile X-ray imaging system, first location information of a first reconstruction volume based on a first sequence of X-ray images of a region of interest of a subject acquired along a first trajectory in a first position of an X-ray imaging device is received. Further, a planned second trajectory for acquiring a second sequence of X-ray images in a second position of the X-ray imaging device is received and a resulting second reconstruction volume for the second sequence of X-ray images is calculated. Then, second location information for the second reconstruction volume is determined. Further, a degree of comparability for the first reconstruction volume and the second reconstruction volume is determined based on the first location information and the second location information. An adapted second trajectory is calculated that results in an increased degree of comparability of the first reconstruction volume and the second reconstruction volume. The adapted second trajectory is provided for acquiring the second sequence of X-ray images in the second position of the X-ray imaging device. In an exemplary embodiment, a computer program enabling a processor to carry out the method of the example above is provided.

In an exemplary embodiment, a computer program or program element for controlling an apparatus according to one of the examples above is provided, which program or program element, when being executed by a processing unit, is adapted to perform the method steps of one of the method examples above.

In an exemplary embodiment, a computer readable medium having stored the program element of one of the embodiments above is provided.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for optimizing an X-ray imaging trajectory, the device comprising:
    a processor in communication with memory, the processor configured to:
        receive first location information of a first reconstruction volume based on a first sequence of X-ray images of a region of interest of a subject acquired along a first trajectory in a first position of an X-ray imaging device;
        receive a planned second trajectory for acquiring a second sequence of X-ray images in a second position of the X-ray imaging device;
        calculate a resulting second reconstruction volume for the second sequence of X-ray images;
        determine second location information for the second reconstruction volume;
        determine a degree of comparability for the first reconstruction volume and the second reconstruction volume based on the first location information and the second location information;
        calculate an adapted second trajectory that results in an increased degree of comparability of the first reconstruction volume and the second reconstruction volume; and
        for an optimized X-ray imaging trajectory, provide the adapted second trajectory for acquiring the second sequence of X-ray images in the second position of the X-ray imaging device.

2. The device according to claim 1, wherein the processor is configured to provide the degree of comparability as an overlap degree of the first reconstruction volume and the second reconstruction volume.

3. The device according to claim 2, wherein the overlap degree relates to a degree of a spatial overlap of the first reconstruction volume and the second reconstruction volume.

4. The device according to claim 2, wherein the overlap degree is provided for a predefined diagnostic purpose.

5. The device according to claim 1, wherein, for the first location information, the processor is configured to:
receive the first trajectory and its a spatial location of the first trajectory; and
determine the first reconstruction volume and the first location information of the first reconstruction volume based on the first trajectory and the spatial location of the first trajectory.

6. The device according to claim 1, wherein the processor is configured to;
receive spatial information of the X-ray imaging device during an acquisition of the first sequence of X-ray images along the first trajectory; and
determine the first trajectory based on the spatial information; and
determine the first reconstruction volume.

7. The device according to claim 1, wherein the processor is configured to:
receive a sequence of first images taken by a camera showing the X-ray imaging device during the acquisition of the first sequence of X-ray images along the first trajectory;
determine the first trajectory based on the sequence of images; and
determine the first reconstruction volume.

8. The device according to claim 1,
wherein the first location information comprises first subject-related spatial information in the first position of the X-ray imaging device;
wherein the degree of comparability is provided as an overlap degree of the first reconstruction volume and the second reconstruction volume;
wherein the processor is configured to:
receive second subject-related spatial information in the second position of the X-ray imaging device; and
determine the overlap degree of the first reconstruction volume and the second reconstruction volume in relation to the subject.

9. The device according to claim 1, wherein the processor is configured to:
determine if the degree of comparability is outside of a predetermined range of comparability; and
provide a repositioning indicator configured to indicate that a repositioning of the X-ray imaging device is required.

10. The device according to claim 1, wherein the first position and the second position of the X-ray imaging device relate to an arrangement of the X-ray imaging device in relation to the subject; and
wherein the second position is different from the first position.

11. An X-ray imaging system comprising:
an X-ray imaging device with an X-ray source and an X-ray detector movable along a trajectory to acquire a sequence of X-ray images of a region of interest; and
the device for optimizing an X-ray imaging trajectory according to claim 1;
wherein the X-ray imaging device provides the first sequence of X-ray images of the region of interest of the subject; and
wherein the processor is configured to provide the adapted second trajectory to the X-ray imaging device for acquiring the second sequence of X-ray images in the second position of the X-ray imaging device.

12. The system according to claim 11, wherein the X-ray imaging system is a mobile X-ray system with a base freely movable along a floor surface;
wherein the X-ray imaging device comprises a movable C-arm with the X-ray source and the X-ray detector mounted to opposing ends of the C-arm; and
wherein a drive mechanism is provided for moving the C-arm to move the X-ray source and the X-ray detector along the adapted second trajectory.

13. The system according to claim 11, further comprising at least one optical camera configured to provide a sequence of first images taken showing the X-ray imaging device during the acquisition of the first sequence of X-ray images along the first trajectory; and
wherein the processor is configured to determine the first trajectory based on the sequence of images and the first reconstruction volume.

14. A method for optimizing an X-ray imaging trajectory, the method comprising:
receiving first location information of a first reconstruction volume based on a first sequence of X-ray images of a region of interest of a subject acquired along a first trajectory in a first position of an X-ray imaging device;
receiving a planned second trajectory for acquiring a second sequence of X-ray images in a second position of the X-ray imaging device;
calculating a resulting second reconstruction volume for the second sequence of X-ray images;
determining second location information for the second reconstruction volume;
determining a degree of comparability for the first reconstruction volume and the second reconstruction volume based on the first location information and the second location information;
calculating an adapted second trajectory that results in an increased degree of comparability of the first reconstruction volume and the second reconstruction volume; and
providing the adapted second trajectory for acquiring the second sequence of X-ray images in the second position of the X-ray imaging device, to a display or user interface, or for providing the adapted second trajectory to the X-ray imaging device and acquiring the second sequence of X-ray images in the second position of the X-ray imaging device.

15. The method according to claim 14, further comprising providing the degree of comparability as an overlap degree of the first reconstruction volume and the second reconstruction volume.

16. The method according to claim 14, further comprising:
determining if the degree of comparability is outside of a predetermined range of comparability; and
providing a repositioning indicator configured to indicate that a repositioning of the X-ray imaging device is required.

17. A non-transitory computer-readable storage medium having stored a computer program comprising instructions which, when executed by a processor, cause the processor to:

receive first location information of a first reconstruction volume based on a first sequence of X-ray images of a region of interest of a subject acquired along a first trajectory in a first position of an X-ray imaging device;

receive a planned second trajectory for acquiring a second sequence of X-ray images in a second position of the X-ray imaging device;

calculate a resulting second reconstruction volume for the second sequence of X-ray images;

determine second location information for the second reconstruction volume;

determine a degree of comparability for the first reconstruction volume and the second reconstruction volume based on the first location information and the second location information;

calculate an adapted second trajectory that results in an increased degree of comparability of the first reconstruction volume and the second reconstruction volume; and provide the adapted second trajectory for acquiring the second sequence of X-ray images in the second position of the X-ray imaging device.

18. The non-transitory computer-readable storage medium according to claim 17, wherein the instructions, when executed by the processor, further cause the processor to provide the degree of comparability as an overlap degree of the first reconstruction volume and the second reconstruction volume.

19. The non-transitory computer-readable storage medium according to claim 17, wherein, for the first location information, the instructions, when executed by the processor, further cause the processor to:

receive the first trajectory and a spatial location of the first trajectory; and determine the first reconstruction volume and the first location information of the first reconstruction volume based on the first trajectory and the spatial location of the first trajectory.

20. The non-transitory computer-readable storage medium according to claim 17, wherein the instructions, when executed by processor, further cause the processor to:

determine if the degree of comparability is outside of a predetermined range of comparability; and provide a repositioning indicator configured to indicate that a repositioning of the X-ray imaging device is required.

* * * * *